United States Patent [19]

Inaba et al.

[11] Patent Number: 5,206,425
[45] Date of Patent: Apr. 27, 1993

[54] PROCESS FOR PREPARING PERPROPIONIC ACID SOLUTION

[75] Inventors: Yukio Inaba; Takafumi Hirakawa; Yohsuke Ueno; Suzuo Takiguchi, all of Ube, Japan

[73] Assignee: Ube Industries, Ltd., Ube, Japan

[21] Appl. No.: 669,755

[22] Filed: Mar. 15, 1991

[30] Foreign Application Priority Data

Mar. 20, 1990 [JP] Japan .................. 2-68374

[51] Int. Cl.$^5$ .......................... C07C 409/24
[52] U.S. Cl. .......................... 562/6; 560/302
[58] Field of Search .................. 562/6; 560/302

[56] References Cited

U.S. PATENT DOCUMENTS

| | | | |
|---|---|---|---|
| 3,264,346 | 8/1966 | Weiberg | 562/6 |
| 4,267,124 | 5/1981 | Hardy et al. | 562/6 |
| 4,338,260 | 7/1982 | Schirmann | 562/6 |
| 5,098,607 | 3/1992 | Inaba et al. | 562/3 |

Primary Examiner—Jose' G. Dees
Assistant Examiner—B. Frazier
Attorney, Agent, or Firm—Frishauf, Holtz, Goodman & Woodward

[57] ABSTRACT

A process for preparing perpropionic acid solution comprising reacting propionic acid with hydrogen peroxide in the presence of a boric acid catalyst wherein the reaction is carried out by using an ethyl propionate as a reaction solvent, and water in the reaction solution is removed continuously by azeotropic distillation with the reaction solvent. Since the reaction is carried out while the concentration of the peroxide in an aqueous phase separated from the distillate by the azeotropic distillation is maintained at not more than 0.1% by weight, a perpropionic acid solution containing almost no unreacted hydrogen peroxide can be prepared.

25 Claims, 1 Drawing Sheet

PROCESS FOR PREPARING PERPROPIONIC ACID SOLUTION

BACKGROUND OF THE INVENTION

The present invention relates to a process for preparing perpropionic acid which is used for, e.g., epoxidation, hydroxylation, formation of lactone, formation of quinone, ring opening of an aromatic ring, formation of phenols, oxidation of a ketone and the like. More specifically, it relates to a process for preparing perpropionic acid by reacting propionic acid with hydrogen peroxide in an alkyl propionate as a reaction solvent which is feasible to form a heterogeneous azeotrope with water in the presence of a catalyst, while continuously removing water introduced with the hydrogen peroxide and water produced during the reaction by azeotropic distillation with the reaction solvent, and keeping a concentration of a peroxide in an aqueous phase separated from liquid distillated by the azeotropic distillation not more than 0.1% by weight.

When perpropionic acid is prepared by a reaction of propionic acid with hydrogen peroxide in the presence of an appropriate catalyst, it is necessary to carry out the reaction while removing (a) the water introduced with the hydrogen peroxide for shifting the reaction, which is an equilibrium reaction, to a system for formation and (b) the water produced during the reaction. It has been proposed as the known prior art to continuously remove the water by azetropic distillation in the presence of "an inert organic solvent which may form a heterogeneous azeotropic mixture with water (hereinafter, merely abbreviated as a "reaction solvent")", for example, an organo-chlorine type solvent such as 1,2-dichloroethane, 1,2-dichloropropane, chloroform, carbon tetrachloride, dichloromethane or the like, or a hydrocarbon type solvent such as benzene, toluene, cyclohexane or the like (see, e.g., Japanese Provisional Patent Publication No. 160313/1979, Japanese Patent Publication No. 64425/1988, Japanese Patent Publication No. 64426/1988, U.S. Pat. No. 2,877,266, U.S. Pat. No. 2,814,641, etc.).

However, the aforementioned methods involve the following defects:

(1) When the water is continuously removed by azeotropic distillation in the reaction in progress, a considerable amount of the peroxides are distilled in the form of unaltered hydrogen peroxide and/or perpropionic acid with an aqueous phase to be removed by distillation to cause a loss of the peroxide. Moreover, in a distillation column where a stabilizer added to the reaction system substantially does not exert the effect, the peroxides will be decomposed to cause a loss. Accordingly, a conversion rate of the hydrogen peroxide and selective reactivity to perpropionic acid are lowered to be unsatisfactory for the utilization in industry.

(2) Where an organo-chlorine type solvent such as 1,2-dichloroethane, 1,2-dichloropropane etc. is used as a reaction solvent, the use of austenitic stainless steel generally used as a material for apparatus may cause troubles such as stress corrosion.

(3) When an organic chlorine type solvent such as 1,2-dichloroethane is used, a catalyst such as a boric acid type catalyst separates out so much times after completion of the reaction. It is necessary to filter and separate the catalyst and the apparatus becomes complex. There is also a problem that the danger due to the adsorption of peroxides is increased.

Further, as a process for solving the aforementioned defect (1), there has been proposed to prevent decomposition of the peroxide and the loss of the peroxide to the aqueous phase by injecting continuously water and propionic acid into a distillation column from the head for inhibiting the rise of the peroxide in the distillation column (for example, Japanese Provisional Patent Publication No. 113173/1983, Japanese Provisional Patent Publication No. 159365/1988, etc.).

Although this method is excellent in view of improvement of a conversion rate of hydrogen peroxide and selective reactivity to produce the perpropionic acid, the following problems still remain unsolved.

That is, where water is injected into the distillation column from the head, it is necessary to further remove the injected water in addition to the water introduced with hydrogen peroxide and the water produced in the reaction resulting in problems a disadvantageous energy consumption and the need for a complicated apparatus.

Also, where propionic acid is injected from the head of column, in addition to the above problem, there is problem that, for example, when $\epsilon$-caprolactone is prepared by using perpropionic acid as the product, the amount of propionic acid is gradually increased with respect to a reaction solvent and whereby separation of the reaction solvent from the propionic acid is required at some point of time in view of recycling of the propionic acid and reaction solvent.

As for the aforementioned defects (2) and (3), it is possible to solve them by purifying the reaction solvent and using a high grade stainless steel. However, it is not a satisfactory process in industry due to the complexity of the apparatus.

SUMMARY OF THE INVENTION

An object of the present invention is to provide a process for preparing perpropionic acid in a high selectivity and in a high yield which can avoid the problems involved in well-known methods for preparing perpropionic acid.

The present inventors have eagerly studied to solve the aforementioned problems and finally attained the present invention.

That is, the present invention is a process for preparing perpropionic acid comprising reacting propionic acid with hydrogen peroxide in the presence of a catalyst wherein the reaction is carried out by using an alkyl propionate as a reaction solvent and water in the reaction solution is removed continuously by an azeotropic distillation with the reaction solvent, and in said azeotropic distillation, said reaction is carried out maintaining a concentration of said peroxide in an aqueous phase of the distillate of not more than 0.1% by weight.

DESCRIPTION OF THE PREFERRED EMBODIMENTS

Figure 1:
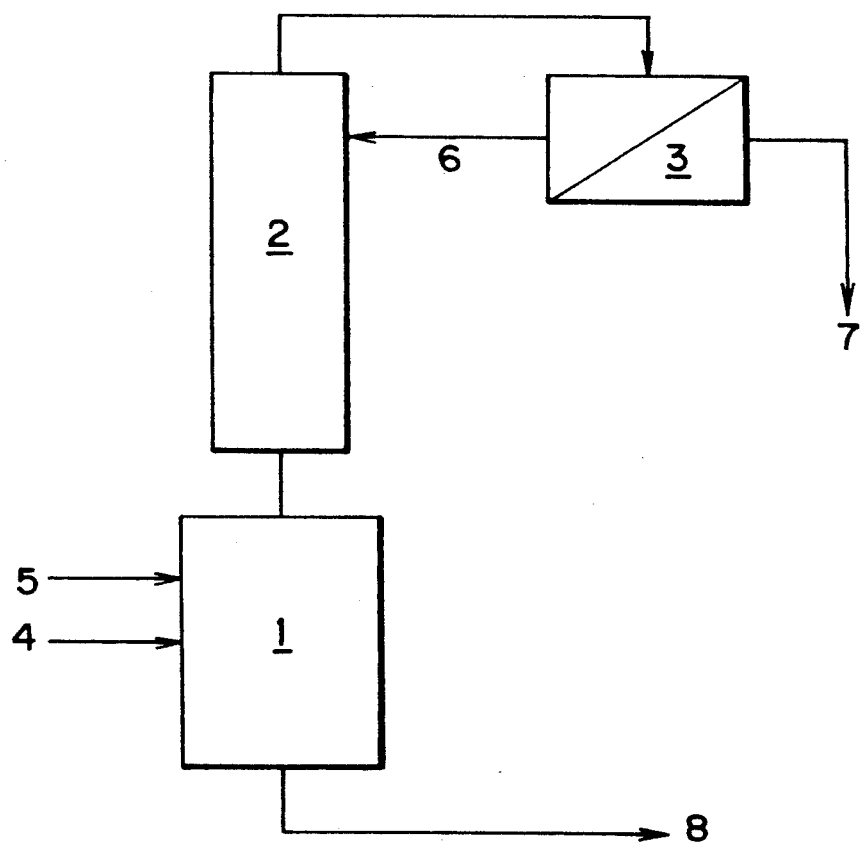
FIG. 1 shows a schematic flow chart of one example of an experimental apparatus to practice the process according to the present invention.

The characteristic features of the present invention comprise, in a process for preparing a substantially anhydrous solution containing perpropionic acid by reacting propionic acid with hydrogen peroxide in the presence of an alkyl propionate which can form a heterogeneous azeotropic mixture with water and a catalyst, removing continuously water, which is introduced with hydrogen peroxide, and water, which is produced upon the reaction by azeotropic distillation in the reaction and keeping the concentration of peroxides consisting of hydrogen peroxide and/or perpropionic acid in the aqueous phase distilled during the course of the reaction at not more than 0.1% by weight, preferably at not more than 200 ppm by weight, particularly preferably at substantially zero. In this instance, "substantially zero" means that the concentration of hydrogen peroxide and perpropionic acid in the aqueous phase of the distillate, determined by the "cerium sulfate titration method" and "thiosulfuric acid titration method" described below, is not more than the detectable limit.

As for a method for removing water continuously during the the reaction by azeotropic distillation, there is no particular limitation. For example, a method in which, in an azeotropic distillation column equipped with a condenser and a decantor, the above-mentioned reaction solvent and water are azeotropically distilled, the distillate condensed by the condenser is introduced into a decantor, and, after separating an organic phase from an aqueous phase by decantation, only the organic phase is refluxed in the azeotropic distillation column, followed by continuous draining of the aqueous phase. Therefore, it is required to keep the peroxide concentration in the aqueous phase separated by decantation in the decantor within the above-mentioned range.

The above-mentioned "peroxide concentration in an aqueous phase of the distillate" becomes possible by selecting various factors such as the concentration and the supplied amount of hydrogen peroxide supplied in the reaction operation and the azeotropic distillation operation, a molar ratio of propionic acid and hydrogen peroxide, kind and employed amount of a catalyst, kind and employed amount of the reaction solvent, reaction temperature, reaction pressure, type of the azeotropic distillation column, reflux ratio of an organic phase in the distillation column, distillation temperature of azeotrope, and the like. Accordingly, in the process of the present invention, it is preferable that the method for keeping the peroxide concentration of the aqueous phase of the distillate within the above-mentioned range may be made by appropriately selecting the supplying speed of hydrogen peroxide, a molar ratio of propionic acid and hydrogen peroxide, an employed amount of a catalyst, an employed amount of the reaction solvent, reaction temperature, reaction pressure and the like within the range as hereinafter provided.

Propionic acid and hydrogen peroxide to be used in the present invention is available in the form of a standard commercial product. Particularly, hydrogen peroxide is commercially available in the form of an aqueous solution containing 30 to 70% by weight thereof. It is preferable that the molar ratio of propionic acid to hydrogen peroxide is in a range of molar ratio of from 1.5 to 6.0 in order to react hydrogen peroxide effectively.

In the present invention, the supplying speed of hydrogen peroxide is about 1 to 100 mg/min/g (ethyl propionate), in particular most preferably about 5 to 50 mg/min/g (ethyl propionate).

The catalyst used in the present invention may include sulfuric acid, hydrochloric acid, phosphoric acid, boric acid, an inorganic or organic acid such as various kinds of sulfonic acid, or cation-exchange resin. These catalysts may be used singly or in combination of two or more of them.

Where the produced perpropionic acid is used, for example, for the production of $\epsilon$-caprolactone, a preferred catalyst is boric acid, i.e., orthoboric acid or metaboric acid to prevent an undesired side reaction such as decomposition or polymerization of the desired product.

An amount of the catalyst employed is 0.001 to 1.0 mole, preferably 0.003 to 0.5 mole, particularly preferably 0.005 to 0.1 mole, and more preferably 0.006 to 0.04 mole per mole of hydrogen peroxide.

The alkyl propionates used in the present invention may include esters prepared from propionic acid and a saturated aliphatic monohydric alcohol containing 1 to 5 carbon atoms, such as methanol, ethanol, 1-propanol, isopropanol, 1-butanol, isobutanol, 1-pentanol and the like; preferably esters prepared from propionic acid and a saturated aliphatic monohydric alcohol containing 1 to 3 carbon atoms; and particularly preferably ethyl propionate being free from an accumulation of impurities is used.

The used amount of alkyl propionate is 0.3 to 15 fold by weight of alkyl propionate with respect to the total amount of water introduced in the reaction system with hydrogen peroxide and water produced in the reaction in order to carry out azeotropic distillation effectively with water coexisting in the reaction system In the method of the present invention, the reaction is preferably carried out at a temperature from 50° to 80° C. The production of the perpropionic acid is slow at a temperature of less than 50° C., while the decomposition loss of the produced perpropionic acid is large at a temperature of more than 80° C., accordingly, both cases undesirably decrease the yield. On the other hand, the reaction may be carried out under different pressures depending on the composition in the reaction system and the selected temperature, but usually under a reduced pressure of 10 to 300 mmHg, particularly preferably 40 to 80 mmHg.

It is most preferable to carry out the reaction under the condition of the combination of the used amount of the above-mentioned preferable alkyl propionate, reaction temperature and reaction pressure in order to maintain the concentration of peroxides in an aqueous phase distilled not more than 0.1% by weight.

Furthermore, the reaction according to the present invention is preferably carried out in the presence of about 0.005 to 1.0%, particularly 0.01 to 0.8% of a stabilizer in order to lower the loss due to the decomposition of the perpropionic acid by a trace amount of metal. Examples of such stabilizer may include a stabilizer such as phosphate, phosphoric acid ester, picolinic acid, dipicolinic acid, etc. and a stabilizer, which is proposed by the present inventor in Japanese Patent Application No. 317702/1989, comprising pyridine derivatives such as picoline, lutidine, or N-oxide thereof, etc.

Perpropionic acid thus obtained may be used for usual epoxidation, hydroxylation, formation of a lactone, ring opening reaction of an aromatic nucleus, formation of a phenol, oxidation of a ketone and the like without problem.

The reaction and azeotropic distillation according to the present invention may be performed by using either continuous or batch operation, preferably the batch operation.

EXAMPLES

The present invention will be described in more detail by referring to Examples and Comparative examples herein-below However, the present invention is not limited to the Examples within the gist of the present invention.

In Examples and Comparative examples, the concentration of hydrogen peroxide and perpropionic acid were determined by "cerium sulfate titration method" and "thiosulfuric acid titration method", respectively.

EXAMPLE 1

Perpropionic acid was prepared by using an experimental apparatus illustrated by a flow chart shown in FIG. 1.

In a 2-liter glass reactor (1) equipped with a distillation column (2) with 20 sheets of oldershow plates and a reflux condenser (3) with a settler were placed 661 g of a solution (4) consisting of 504 g of propionic acid, 150 g of ethyl propionate, 6.4 g of orthoboric acid and 0.6 g of 2-picoline as a stabilizer.

Then, the reactor (1) was immersed in an oil bath and heated up to 100° C. The solution (4) was heated to the boiling point under reflux at a reduced pressure of 60 mmHg and 107.4 g of 60 wt % of hydrogen peroxide (5) as a whole were added over 30 minutes. The temperature of the solution in the reactor (1) was about 65° C. An organic phase (6) formed by a condensed heterogeneous azeotrope was recycled through the reflux condenser (3) provided to allow the reflux with a settler. On the other hand, the condensed aqueous phase (7) was continuously separated from the reflux condenser (3) with a settler.

After the propionic acid and hydrogen peroxide were reacted until the separation of the aqueous phase (7) in the reflux condenser (3) provided with the settler could not substantially be seen, heating of the reactor (1) was stopped to yield 671 g of a perpropionic acid solution (8). The reaction time was two hours and a half from the start of addition of the hydrogen peroxide.

The result is shown in Table 1.

EXAMPLE 2

The same procedure as in Example 1, was repeated provided that the amount of orthoboric acid from 6.4 g to 1.6 g to obtain 680 g of a perpropionic acid solution (8). The reaction time was three hours and a half from the start of addition of hydrogen peroxide.

The result is shown in Table 1.

COMPARATIVE EXAMPLE 1

The same procedure as in Example 1 was repeated provided that 136 g of 1,2-dichloroethane was used instead of ethyl propionate and the pressure was changed to 100 mmHg (inner temperature: 65° C.) to obtain 670 g of a perpropionic acid solution (8). The reaction time was three hours from the start of addition of hydrogen peroxide.

The result is shown in Table 1.

COMPARATIVE EXAMPLE 2

The same procedure as in Example 1 was repeated provided that the amount of orthoboric acid was changed from 6.4 g to 2.2 g to obtain 663 g of a perpropionic acid solution (8). The reaction time was three hours and 45 minutes from the start of addition of hydrogen peroxide.

The result is shown in Table 1.

COMPARATIVE EXAMPLE 3

The same procedure as in Comparative example 1 was repeated provided that distilled water was added at a rate of 20 g/hour over a 2.5 hours period into the distillation column from the head (2) from the start of addition of hydrogen peroxide to obtain 662 g of a perpropionic acid solution (8). The reaction time was 3 hours from the start of addition of hydrogen peroxide. In this Comparative example, it was required to remove by evaporation other than the water introduced with hydrogen peroxide and produced in the reaction, "distilled water injected into the head of a distillation column", whose amount was about 65% by weight of those of the above two kinds of waters, whereby the amount of energy consumption became enormous and the operation became troublesome.

The result is shown in Table 1.

TABLE 1

|  |  | Example 1 | Example 2 | Compa. example 1 | Compa. example 2 | Compa. example 3 |
|---|---|---|---|---|---|---|
| Amount of hydrogen peroxide supplied | mole | 1.90 | 1.90 | 1.90 | 1.90 | 1.90 |
| Amount of orthoboric acid supplied | mole | 0.10 | 0.03 | 0.10 | 0.04 | 0.10 |
| Separated aqueous phase | | | | | | |
| Amount of hydrogen peroxide | mole | 0.00 | 0.00 | 0.06 | 0.10 | 0.01 |
| Amount of perpropionic acid | mole | 0.00 | 0.00 | 0.01 | 0.01 | 0.00 |
| Perpropionic acid solution | | | | | | |
| Amount of hydrogen peroxide | mole | 0.02 | 0.01 | 0.04 | 0.03 | 0.03 |
| Amount of perpropionic acid | mole | 1.80 | 1.78 | 1.68 | 1.63 | 1.79 |
| Unreacted rate of hydrogen peroxide | % | 1.1 | 0.5 | 5.3 | 6.8 | 2.1% |
| Selection rate of perpropionic acid | % | 95.9 | 94.2 | 93.9 | 92.6 | 96.2 |
| Yield of perpropionic acid | % | 94.8 | 93.7 | 88.9 | 86.3 | 94.2 |
| Loss rate of peroxide into an | % | 0.0 | 0.0 | 3.7 | 5.8 | 0.5 |

EXAMPLES 3 TO 5

The procedures were carried out in the same manner as in Example 2 to prepare a solution of perpropionic acid (8) respectively in the amount as shown in Table 2 except for changing the used amount of ethyl propionate and the used amount of 2-picoline to the amount as shown in Table 2 and changing the reaction time to 4 hours. Other results are shown in Table 2 respectively.

TABLE 2

|  |  | Example 3 | Example 4 | Example 5 |
|---|---|---|---|---|
| Amount of propionic acid supplied | mole | 6.80 | 6.80 | 6.80 |
| Used amount of ethyl propionate | g | 150 | 120 | 118 |
| Amount of hydrogen peroxide supplied | mole | 1.90 | 1.90 | 1.90 |
| Used amount of 2-picoline | g | 0.3 | 1.2 | 3.0 |
| Amount of orthoboric acid supplied | mole | 0.03 | 0.03 | 0.03 |
| Reaction |  |  |  |  |
| Pressure | mmHg | 60 | 60 | 60 |
| Reaction temperature | °C. | 65 | 65 | 65 |
| Added time of hydrogen peroxide | minute | 30 | 30 | 30 |
| Reaction time | hour | 4.0 | 4.0 | 4.0 |
| Amount of a perpropionic acid solution | g | 679 | 647 | 644 |
| Separated aqueous phase |  |  |  |  |
| Amount of hydrogen peroxide | mole | 0.00 | 0.00 | 0.00 |
| Amount of perpropionic acid | mole | 0.00 | 0.00 | 0.00 |
| Perpropionic acid solution |  |  |  |  |
| Amount of hydrogen peroxide | mole | 0.01 | 0.02 | 0.01 |
| Amount of perpropionic acid | mole | 1.78 | 1.77 | 1.75 |
| Unreacted rate of hydrogen peroxide | % | 0.6 | 0.9 | 0.4 |
| Selection rate of perpropionic acid | % | 94.5 | 94.2 | 92.7 |
| Yield of perpropionic acid | % | 93.9 | 93.4 | 92.3 |
| Loss rate of peroxide into an aqueous phase | % | 0.0 | 0.0 | 0.0 |

EXAMPLES 6 AND 7

The procedures were carried out in the same manner as in Example 2 to prepare a solution of perpropionic acid in the amount shown in Table 3 except for changing the used amount of ethyl propionate and the used amount of orthoboric acid and changing the reaction time to those shown in Table 3. Other results are shown in Table 3 respectively.

EXAMPLES 8 TO 10

The procedure were carried out in the same manner as in Example 2 to prepare a solution of perpropionic acid in the amount shown in Table 3 except for changing the used amount of propionic acid and ethyl propionate, the reaction pressure and the reaction time to those shown in Table 3 (in Example 8, a molar ratio of propionic acid/hydrogen peroxide is 3.80, in Example 9, a molar ratio of propionic acid/hydrogen peroxide is 3.95 and in Example 10, a molar ratio of propionic acid/hydrogen peroxide is 4.09). Other results are shown in Table 3 respectively.

TABLE 3

|  |  | Example 6 | Example 7 | Example 8 | Example 9 | Example 10 |
|---|---|---|---|---|---|---|
| Amount of propionic acid supplied | mole | 6.80 | 6.80 | 7.21 | 7.48 | 7.75 |
| Used amount of ethyl propionate | g | 154 | 152 | 93 | 70 | 53 |
| Amount of hydrogen peroxide supplied | mole | 1.90 | 1.90 | 1.90 | 1.90 | 1.90 |
| Used amount of 2-picoline | g | 0.6 | 0.6 | 0.6 | 0.6 | 0.6 |
| Amount of orthoboric acid supplied | mole | 0.05 | 0.01 | 0.03 | 0.03 | 0.03 |
| Reaction |  |  |  |  |  |  |
| Pressure | mmHg | 60 | 60 | 52 | 45 | 40 |
| Reaction temperature | °C. | 65 | 65 | 65 | 65 | 65 |
| Added time of hydrogen peroxide | minute | 30 | 30 | 30 | 30 | 30 |
| Reaction time | hour | 4.0 | 5.0 | 4.0 | 4.0 | 4.0 |
| Amount of a perpropionic acid solution | g | 685 | 682 | 649 | 645 | 652 |
| Separated aqueous phase |  |  |  |  |  |  |
| Amount of hydrogen peroxide | mole | 0.00 | 0.00 | 0.00 | 0.00 | 0.00 |
| Amount of perpropionic acid | mole | 0.00 | 0.00 | 0.00 | 0.00 | 0.00 |
| Perpropionic acid solution |  |  |  |  |  |  |
| Amount of hydrogen peroxide | mole | 0.01 | 0.01 | 0.01 | 0.01 | 0.01 |
| Amount of perpropionic acid | mole | 1.78 | 1.75 | 1.78 | 1.79 | 1.78 |
| Unreacted rate of hydrogen peroxide | % | 0.3 | 0.3 | 0.5 | 0.4 | 0.5 |
| Selection rate of perpropionic acid | % | 94.4 | 92.5 | 94.6 | 94.6 | 94.3 |
| Yield of perpropionic acid | % | 94.1 | 92.2 | 94.1 | 94.2 | 93.8 |
| Loss rate of peroxide into | % | 0.0 | 0.0 | 0.0 | 0.0 | 0.0 |

TABLE 1-continued

|  | Example 1 | Example 2 | Compa. example 1 | Compa. example 2 | Compa. example 3 |
|---|---|---|---|---|---|
| aqueous phase |  |  |  |  |  |

Note: In the table, the yield (%) of perpropionic acid and the loss rate (%) of peroxide into an aqueous phase are based on the amount of supplied hydrogen peroxide. Peroxide means the sum of hydrogen peroxide and perpropionic acid. The above footnote applies in the same manner in following Tables 2 and 3.

TABLE 3-continued

|  | Example 6 | Example 7 | Example 8 | Example 9 | Example 10 |
|---|---|---|---|---|---|
| an aqueous phase |  |  |  |  |  |

According to the present invention in preparation of perpropionic acid from propionic acid and hydrogen peroxide, water in the reaction solution can be easily removed by the azeotropic distillation with an alkyl propionate and, the preparation can be carried out without continuous injection of water and propionic acid into the distillation column from the head and the loss of unaltered hydrogen peroxide and/or perpropionic acid can be prevented. Thus, the desired product can be obtained effectively at high yield. Also manufacturing apparatus for this process can be prepared by use of a material having average grade such as austenitic stainless steel. Therefore, the process is valuable in industrial utilization.

Further in the present invention, the amount of a catalyst used in the reaction can be decreased. As a result, since the boric acid catalyst does not separate out after completion of the reaction, the filtration separation is not also required and the apparatus becomes simple. Moreover, the danger due to the adsorption of peroxides in the operation of the filtration separation can be avoided.

We claim:

1. A process for preparing perpropionic acid solution comprising (a) reacting propionic acid with hydrogen peroxide in the presence of a boric acid catalyst, at least one stabilizer selected from the group consisting of picolinic acid, dipicolinic acid, 2-picoline, rutidine and an N-oxide thereof, and a reaction solvent to form a reaction solution, wherein the reaction solvent is ethyl propionate, (b) continuously removing water from the reaction solution by an azeotropic distillation with the reaction solvent, said azeotropic distillation resulting in a distillate comprising an aqueous phase and (c) maintaining a concentration of said peroxide in the aqueous phase of the distillate of not more than 0.1% by weight.

2. The process of claim 1 wherein the amount of said ethyl propionate is 0.3 to 15 fold by weight with respect to the total amount of water introduced in the reaction solution with hydrogen peroxide and water produced in the reaction.

3. The process of claim 1 wherein the reaction is carried out at a temperature of 50° to 80° C.

4. The process of claim 1 wherein the molar ratio of propionic acid/hydrogen peroxide is 1.5 to 6.0.

5. The process of claim 1 wherein the supplying speed of said hydrogen peroxide is about 1 to 100 mg/min/g (ethyl propionate).

6. The process of claim 5 wherein the supplying speed of said hydrogen peroxide is about 5 to 50 mg/min/g (ethyl propionate).

7. The process of claim 1 wherein the added amount of said catalyst is 0.001 to 1.0 mole per 1 mole of hydrogen peroxide.

8. The process of claim 7 wherein the added amount of said catalyst is 0.003 to 0.5 mole per 1 mole of hydrogen peroxide.

9. The process of claim 8 wherein the added amount of said catalyst is 0.005 to 0.1 mole per 1 mole of hydrogen peroxide.

10. The process of claim 9 wherein the added amount of said catalyst is 0.006 to 0.04 mole per 1 mole of hydrogen peroxide.

11. The process of claim 1 wherein the reaction is carried out at a pressure of 10 to 300 mmHg 12. The process of claim 11 wherein the reaction pressure is 40 to 80 mmHg.

13. The process of claim 1 wherein the concentration of the peroxide is not more than 200 ppm.

14. The process of claim 13 wherein the concentration of the peroxide is substantially zero.

15. The process of claim 1 wherein said stabilizer is at least one selected from the group consisting of 2-picoline, rutidine and N-oxides thereof.

16. The process of claim 1 wherein the amount of the stabilizer is about 0.005 to 1.0% with respect to the weight of the perpropionic acid solution.

17. The process of claim 16 wherein the amount of the stabilizer is 0.01 to 0.8% with respect to the weight of the perpropionic acid solution.

18. The process of claim 1 wherein the reaction is carried out at a pressure of 10 to 300 Hg and at a temperature of 50° to 80° C.

19. The process of claim 2, wherein said boric acid is selected from the group consisting of orthoboric acid and metaboric acid.

20. The process of claim 19, wherein the reaction is carried out at a temperature of 50° to 80° C.

21. The process of claim 20, wherein the added amount of said catalyst is 0.006 to 0.04 mole per 1 mole of hydrogen peroxide and the molar ratio of propionic acid to hydrogen peroxide is 1.5 to 6.0.

22. The process of claim 21, wherein the reaction is carried out at a pressure of 40 to 80 mmHg.

23. The process of claim 22 wherein the concentration of peroxide is not more than 200 ppm.

24. The process of claim 23, wherein the amount of the stabilizer is 0.01 to 0.8 with respect to the weight of the perpropionic acid.

25. The process of claim 1, wherein said boric acid is orthoboric acid; said stabilizer is 2-picoline; said ethyl propionate is in an amount of 0.3 to 15 fold by weight with respect to the total amount of water introduced into the reaction with hydrogen peroxide and the water produced in the reaction; the reaction is carried out at a temperature of 50° to 80° C. and at a pressure of 10 to 300 mmHg; said hydrogen peroxide is fed at a rate of 1 to 100 mg/min/g of ethyl propionate; said catalyst is in an amount of 0.001 to 1.0 mole per 1 mole of said hydrogen peroxide; and said stabilizer is in an amount of 0.005 to 1.0% with respect to the weight of the perpropionic acid solution.

* * * * *